US009591286B2

(12) United States Patent
Yun et al.

(10) Patent No.: US 9,591,286 B2
(45) Date of Patent: Mar. 7, 2017

(54) 3D IMAGE CAPTURE APPARATUS WITH DEPTH OF FIELD EXTENSION

(71) Applicant: 3M INNOVATIVE PROPERTIES COMPANY, St. Paul, MN (US)

(72) Inventors: Zhisheng Yun, Woodbury, MN (US); David B. Stegall, Saint Paul, MN (US); Shannon D. Scott, Hudson, WI (US); James L. Graham, II, Woodbury, MN (US); Paul A. Sevcik, White Bear Township, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 286 days.

(21) Appl. No.: 14/277,113

(22) Filed: May 14, 2014

(65) Prior Publication Data

US 2015/0334374 A1    Nov. 19, 2015

(51) Int. Cl.
| H04N 13/02 | (2006.01) |
| G02B 17/08 | (2006.01) |
| G02B 17/02 | (2006.01) |
| H04N 5/225 | (2006.01) |
| G02B 27/22 | (2006.01) |

(52) U.S. Cl.
CPC ........ *H04N 13/0235* (2013.01); *G02B 17/023* (2013.01); *G02B 17/0804* (2013.01); *G02B 27/22* (2013.01); *H04N 5/2252* (2013.01); *H04N 5/2253* (2013.01); *H04N 13/0217* (2013.01)

(58) Field of Classification Search
CPC ............ H04N 13/0235; H04N 13/0217; H04N 5/2253; H04N 5/2252; G02B 17/0804; G02B 17/023; G02B 27/22

USPC .......................................................... 348/46
See application file for complete search history.

(56) References Cited

U.S. PATENT DOCUMENTS

| 7,605,817 B2 | 10/2009 | Zhang |
| 7,646,550 B2 | 1/2010 | Rohaly |
| 7,956,862 B2 | 6/2011 | Zhang |
| D674,091 S | 1/2013 | Carlson |
| 8,842,168 B2 | 9/2014 | Berestov et al. |
| 2007/0164202 A1* | 7/2007 | Wurz ....................... H04N 1/04 250/222.1 |

(Continued)

FOREIGN PATENT DOCUMENTS

| JP | 2002125247 | 4/2002 |
| KR | 100150055 | 12/1998 |

OTHER PUBLICATIONS

English Translation of Japanese Publication 2002-125247, Apr. 2002.*

(Continued)

*Primary Examiner* — William Tran

(57) ABSTRACT

A 3D imaging apparatus with enhanced depth of field to obtain electronic images of an object for use in generating a 3D digital model of the object. The apparatus includes a housing having mirrors positioned to receive an image from an object external to the housing and provide the image to an image sensor. The optical path between the object and the image sensor includes an aperture element having apertures for providing the image along multiple optical channels with a lens positioned within each of the optical channels. The depth of field of the apparatus includes the housing, allowing placement of the housing directly on the object when obtaining images of it.

7 Claims, 7 Drawing Sheets

(56) References Cited

U.S. PATENT DOCUMENTS

| | | |
|---|---|---|
| 2007/0172112 A1 | 7/2007 | Paley |
| 2009/0221874 A1 | 9/2009 | Vinther |
| 2013/0235165 A1* | 9/2013 | Gharib .................... G06T 7/004 348/50 |
| 2015/0062326 A1* | 3/2015 | Startchik ................ G01N 21/84 348/86 |

OTHER PUBLICATIONS

PCT International Search Report for PCT/US2015/027929, mailed Jul. 29, 2015.
Wand Image 1 of an existing intra-oral scanning wand from 3M Company, 1 page, Jul. 2008.
Wand Image 2 of an existing intra-oral scanning wand from 3M Company, 1 page, Jul. 2008.
Wand Image 3 of an existing intra-oral scanning wand from 3M Company, 1 page, Jul. 2008.

* cited by examiner

3D IMAGE CAPTURE APPARATUS WITH DEPTH OF FIELD EXTENSION

BACKGROUND

A multi-channel 3D camera system obtains digital images of an object from multiple view points, which can be used to generate a 3D image of the object. One such 3D camera system is an intra-oral scanner used to generate a 3D digital model of teeth. Using an intra-oral scanner requires a particular positioning to obtain electronic images of the intra-oral structures to accurately generate a corresponding 3D model. Accordingly, there is a need to extend the depth of the field of a 3D camera system to ease the scanning ability in a dental scanner or other types of scanner.

SUMMARY

A first 3D imaging apparatus, consistent with the present invention, includes a housing and an image sensor within the housing. First and second mirrors are positioned to receive an image from an object external to the housing and provide the image to the image sensor, which is positioned substantially parallel to an object plane of the object. An aperture element having a plurality of apertures is located along an optical path between the object and the image sensor for providing the image along a plurality of optical channels to the image sensor.

A second 3D imaging apparatus, consistent with the present invention, includes a housing and an image sensor within the housing. A mirror is positioned to receive an image from an object external to the housing and provide the image to the image sensor, which is positioned substantially perpendicular to an object plane of the object. An aperture element having a plurality of apertures is located along an optical path between the object and the image sensor for providing the image along a plurality of optical channels to the image sensor.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Embodiments of the present invention increase the depth of field of a 3D camera system. The system has multiple optical channels to capture multiple views of an object from varying viewpoints that can be used to generate a 3D image of it. An electronic digital imager sensor captures a scene of a 3D object through the multiple apertures to obtain different view-angle images. Software algorithms can rebuild the 3D scene into a 3D image or model based on the captured different view-angle images of the scene.

Systems to generate 3D images or models based upon image sets from multiple views are disclosed in U.S. Pat. Nos. 7,956,862 and 7,605,817, both of which are incorporated herein by reference as if fully set forth. These systems can be included in a housing providing for hand-held use, and an example of such a housing is disclosed in U.S. Pat. No. D674,091, which is incorporated herein by reference as if fully set forth.

Figure 1:
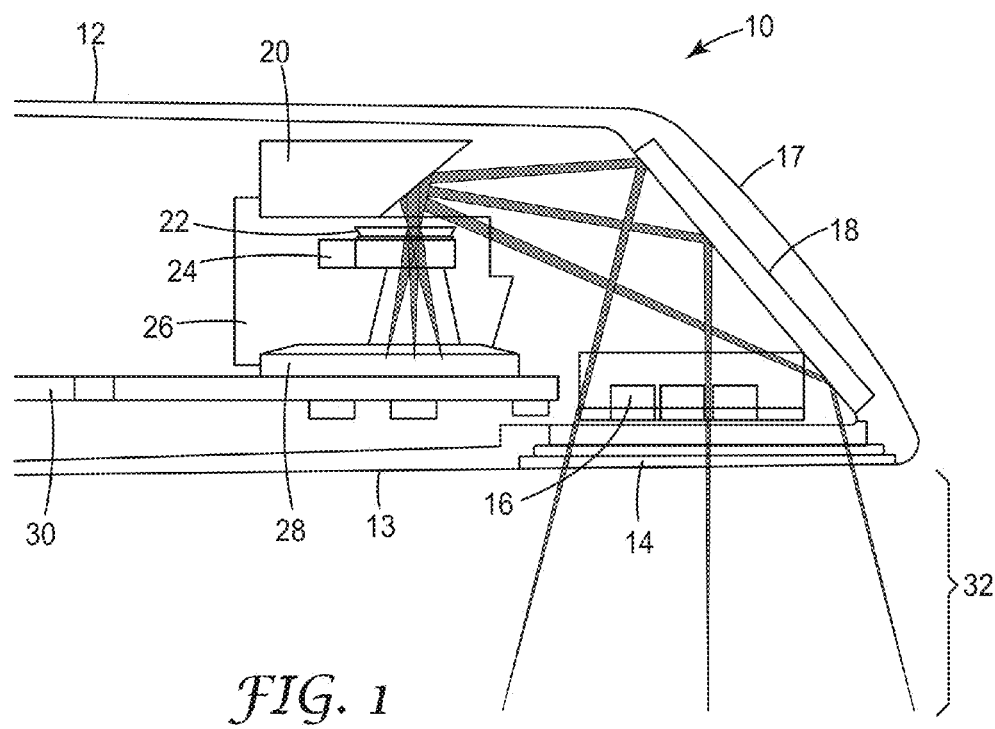
FIG. 1 is a side view of a 3D imager with depth of field extension.

FIG. 1 is a side view of a 3D imager 10 with depth of field extension through the use of two mirrors. System 10 includes a housing 12, mirrors 18 and 20, an aperture element 22, lenses 24, and an image sensor 28. Housing 12 has an angled tip 17 with mirror 18 secured adjacent an interior surface of the tip. A mechanical holder 26 is used to hold mirror 20, aperture element 22, and lenses 24 in position over image sensor 28. A circuit board 30 can receive electronic signals from image sensor 28 representing the images and transmit the signals for further processing to generate a 3D model of the object. Housing 12 includes a transparent cover 14 and light sources 16 adjacent the cover to illuminate an object to be imaged. In this design, image sensor 28 is positioned substantially parallel to an object plane of the object. The imager has a depth of field 32 which includes housing 12, in particular a bottom surface 13 of the housing. The depth of field can alternatively include and extend into the inside of housing 12. By having the depth of field include the housing, imager 10 can be placed directly on (in physical contact with) an object to be imaged, such as on teeth for intra-oral scanning.

Figure 2:
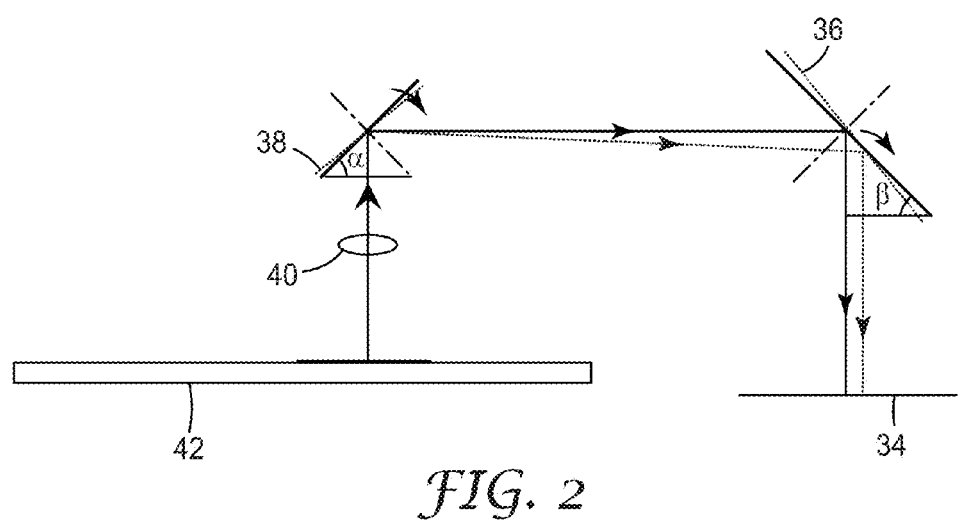
FIG. 2 is a diagram illustrating use of two fold mirrors for depth of field extension.

For the configuration of imager 10 of FIG. 1, the image plane (image sensor surface plane) 42 is positioned along the horizontal plane with object plane 34, as shown in FIG. 2. Mirrors 36 and 38 provide an image of an object at object plane 34 through a lens 40 to an image sensor at image plane 42. If the image sensor surface is normal to the optical axis of lens 40, to achieve good image quality over the entire field of view of object plane 34, object plane 34 needs to be parallel to image plane 42. If α is the angle of mirror 38 to image plane 42 and β is the angle of the mirror 36 to object plane 34, to have a good image quality over the lens field of view, mirrors 36 and 38 have the following relationship: α+β=90°.

FIGS. 1 and 2 show a configuration using two planar fold mirrors. For the two fold mirrors configuration, either of the two fold mirrors, or both of the mirrors, can be implemented with concave mirrors. If concave mirrors are used, the position of the image sensor can be adjusted to compensate for the focus of the concave mirror and obtain sharp images.

Figure 3:
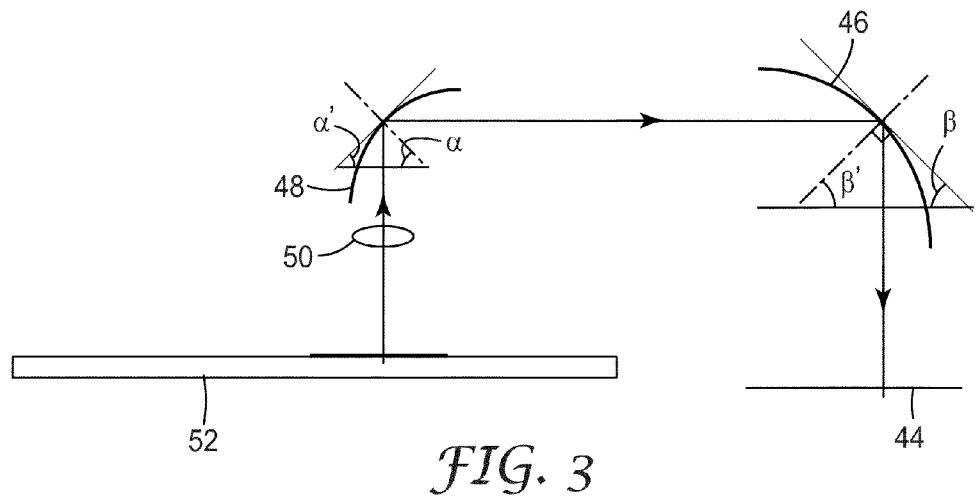
FIG. 3 is a diagram illustrating use of two concave mirrors for depth of field extension.

FIG. 3 illustrates a system using two concave mirrors. Mirrors 46 and 48 provide an image of an object at object plane 44 through a lens 50 to an image sensor at image plane 52. If the image sensor surface is normal to the optical axis of lens 50, to achieve good image quality over the entire field of view of object plane 44, object plane 44 needs to be parallel to image plane 52. If α' is the angle of mirror 48 to image plane 52 and β' is the angle of the mirror 46 to object plane 44, to have a good image quality over the lens field of view, mirrors 46 and 48 have the following relationship: α'+β'=90°.

Figure 4:
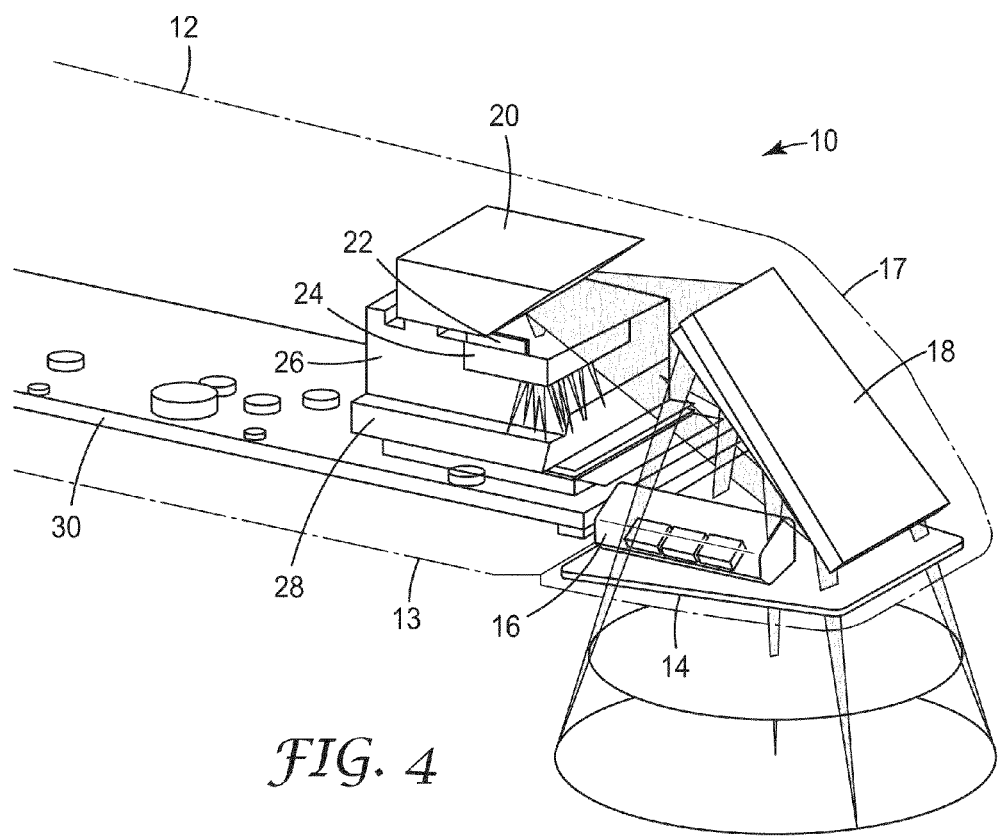
FIG. 4 is a perspective view of the 3D imager of FIG. 1.
Figure 5:
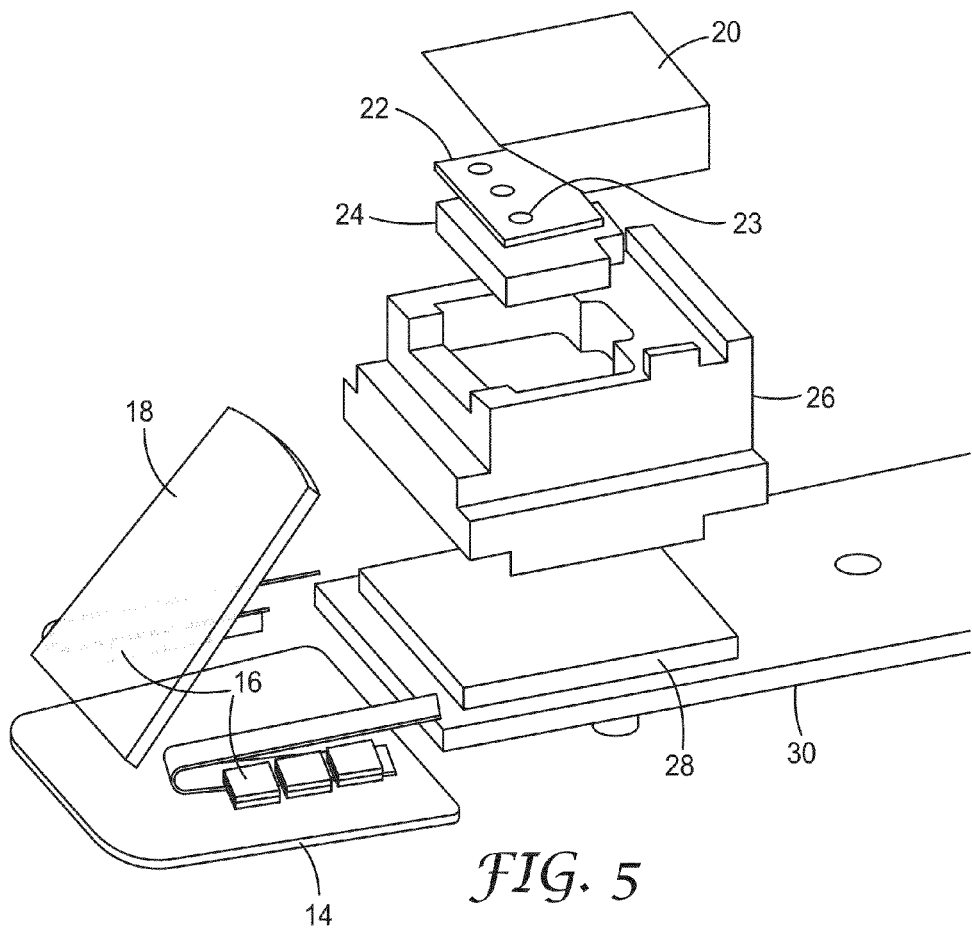
FIG. 5 is an exploded perspective view of the 3D imager of FIG. 1.
Figure 6:
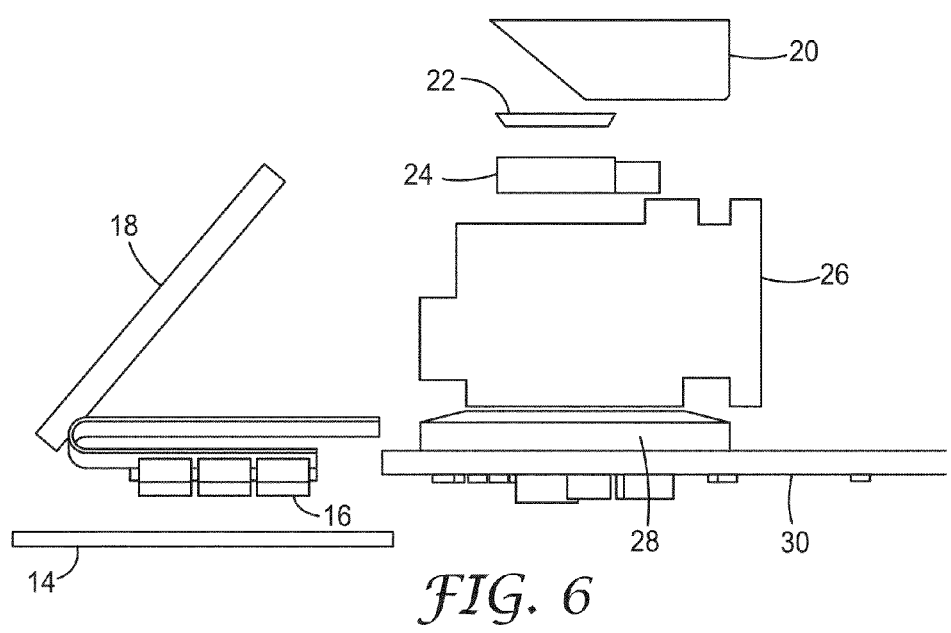
FIG. 6 is an exploded side view of the 3D imager of FIG. 1.

FIGS. 4-6 are perspective, exploded perspective, and exploded side views, respectively, of 3D imager 10 of FIG. 1. FIG. 5 illustrates apertures 23 in aperture element 22 to create multiple channels. Although three apertures are shown, aperture element 22 can alternatively have two apertures for a two channel system.

The components of imager 10 can be implemented with, for example, the following. Mirrors 18 and 20 can be aluminum or silver coated on optical glass or metal. Mirror 18 can alternatively be a prism, and mirror 20 can alternatively be a planar mirror plate. A prism is used for mirror 20 for ease of holding the mirror in place on holder 26. Mirrors 18 and 20 can optionally be one piece of material with mirrors on both ends. Mirrors 18 and 20 are preferably positioned at 50° and 40°, respectively, from the image plane. The angles of the mirrors should total 90° for the image sensor to obtain images normal to the target, and each of the angles can thus be adjusted for desired placement in the housing. Lenses 24 can include separate lenses for each channel or be a single molded piece of material. Exemplary lens arrays are provided below. Aperture element 22 can be a multi-layer metal plate, such as BeCu base with Ni plating, with holes etched into it for the apertures 23. Holder 26 can be aluminum or a molded plastic material, and mirror 20, aperture element 22, and lenses 24 can be adhered to holder 26 or mechanically held in place on the holder. Light sources 16 can be light emitting diodes (LEDs). Cover 14 can be optical glass. Housing 12 can be metal or a plastic material. The various components of imager 10 in housing 12 can be positioned at particular distances in the optical path for a desired performance.

Figure 7:
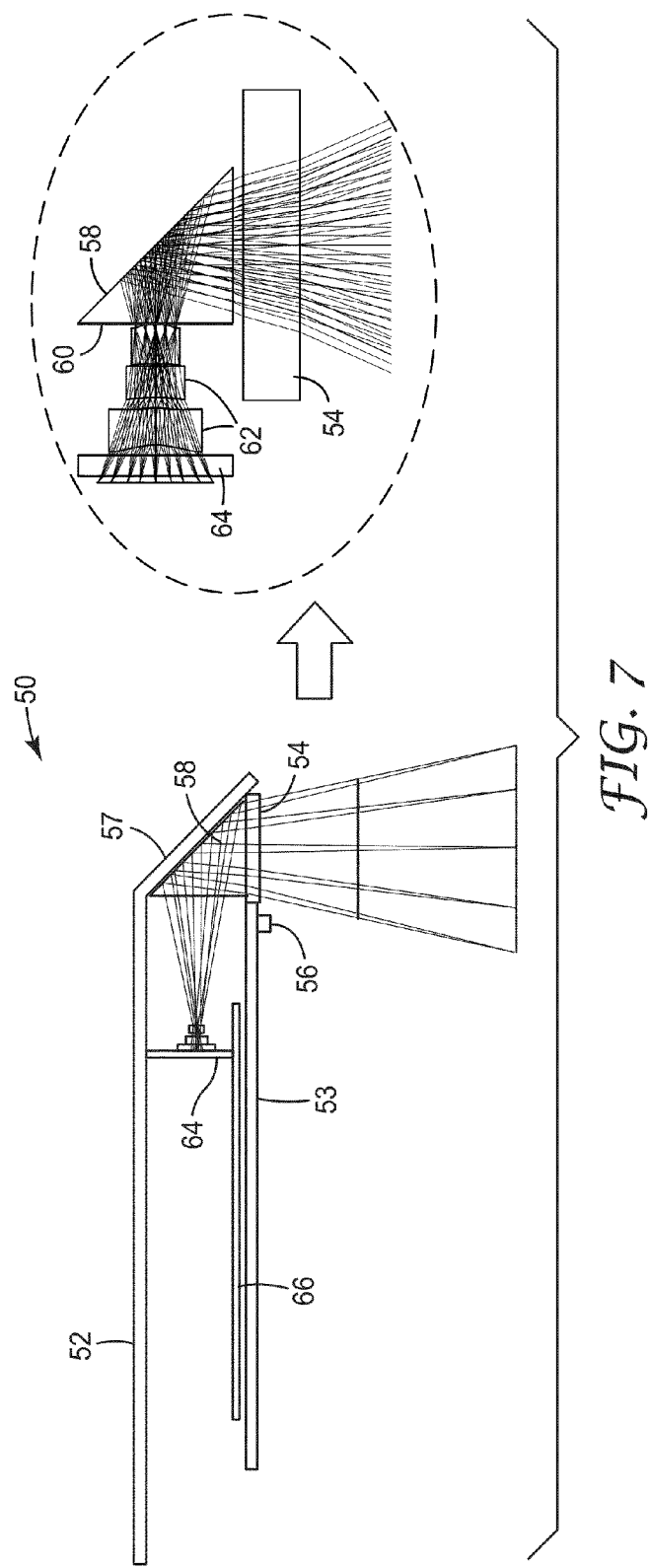
FIG. 7 is a side view of an alternative 3D imager with depth of field extension.
Figure 8:
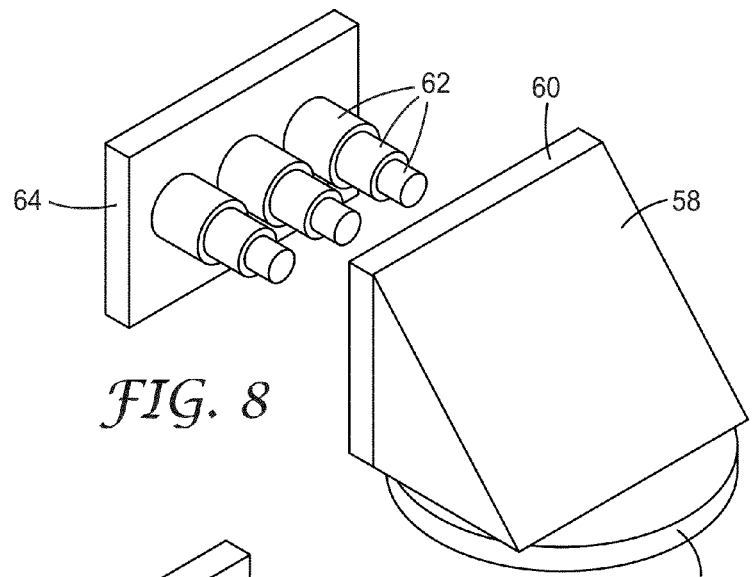
FIG. 8 is a perspective view of the 3D imager of FIG. 7.
Figure 9:
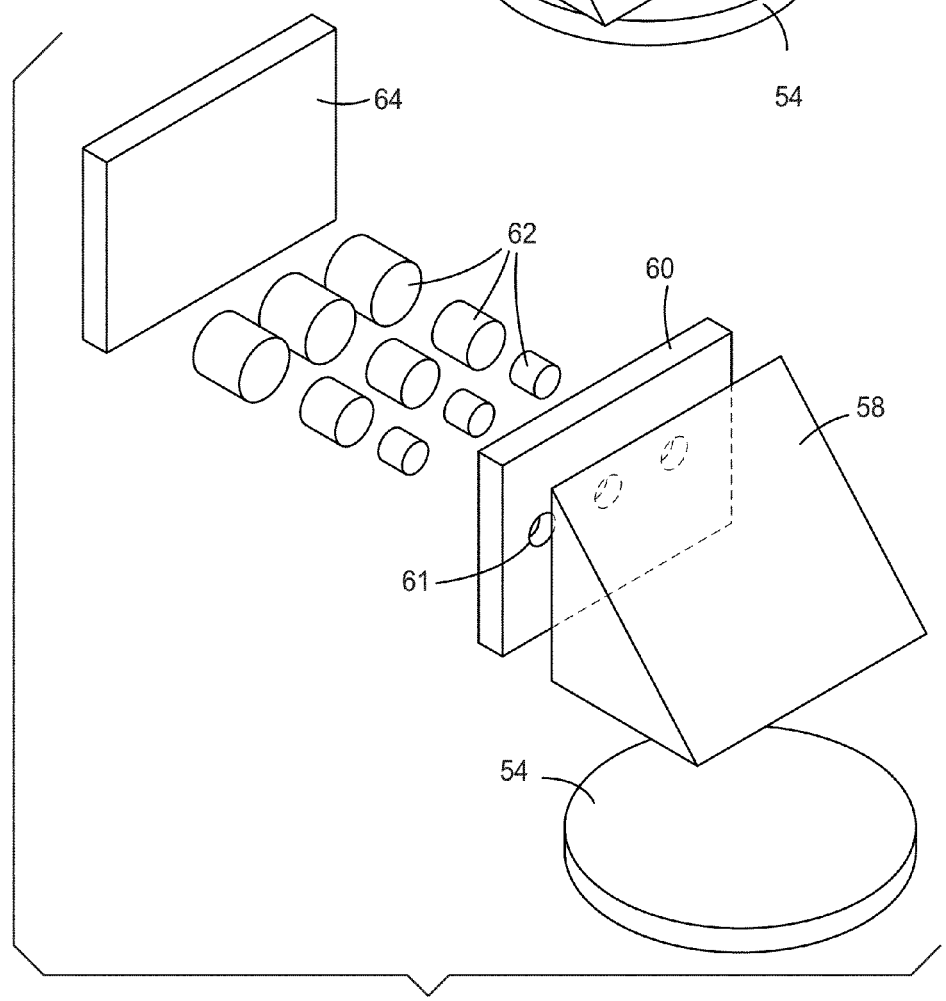
FIG. 9 is an exploded perspective view of the 3D imager of FIG. 7.

FIG. 7 is a side view of an alternative 3D imager 50 with depth of field extension using one fold mirror. FIGS. 8 and 9 are perspective and exploded perspective views, respectively, of 3D imager 50 of FIG. 7. System 50 includes a housing 52, a mirror 58, an aperture element 60, lenses 62, and an image sensor 64. Housing 52 has an angled tip 57 with mirror 58 secured adjacent an interior surface of the tip. A circuit board 66 can receive electronic signals from image sensor 64 representing the images and transmit the signals for further processing to generate a 3D model of the object. Housing 52 includes a transparent cover 54 and light sources 56, such as LEDs, adjacent the cover to illuminate an object to be imaged. In this design, image sensor 64 is positioned substantially perpendicular to an object plane of the object. The imager has a depth of field which includes housing 52, in particular a bottom surface 53 of the housing. The depth of field can alternatively include and extend into the inside of housing 52. By having the depth of field include the housing, imager 50 can be placed directly on (in physical contact with) an object to be imaged, such as on teeth for intra-oral scanning.

FIG. 9 illustrates apertures 61 in aperture element 60 to create multiple channels. Although three apertures are shown, aperture element 60 can alternatively have two apertures for a two channel system. Aperture element 60 can be on prism mirror 58, on lenses 62, or in between mirror 58 and lenses 62 with gaps on both sides of aperture element 60. Lenses 62 can be separate lenses or one molded piece of material for each channel. The fold mirror in imager 50 can be implemented with a concave mirror or a planar mirror plate instead of the prism as shown. The components of imager 50 can be implemented with the exemplary materials provided above for imager 10.

Figure 10:
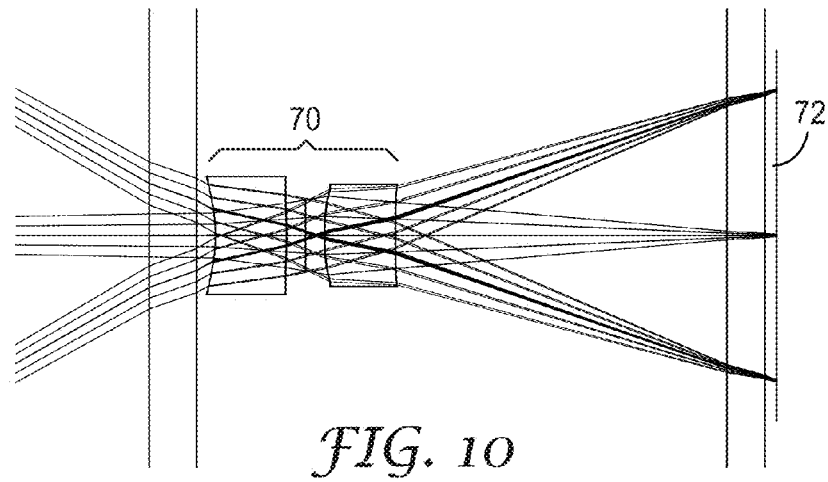
FIG. 10 is a diagram illustrating two optical elements for each optical channel in a 3D imager.
Figure 11:
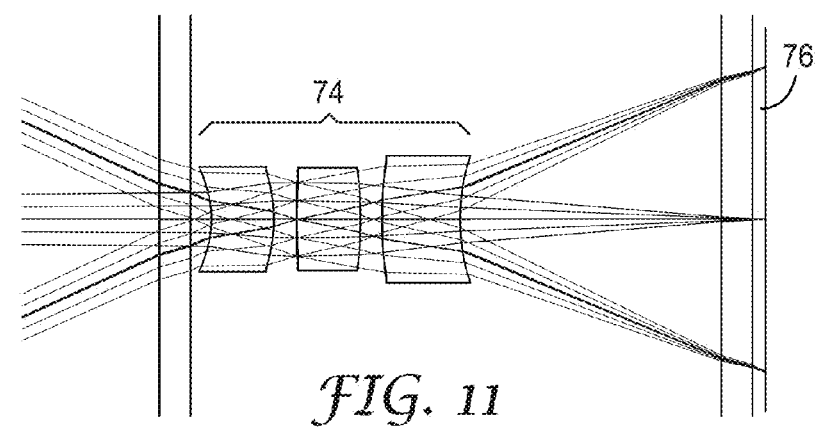
FIG. 11 is a diagram illustrating three optical elements for each optical channel in a 3D imager.
Figure 12:
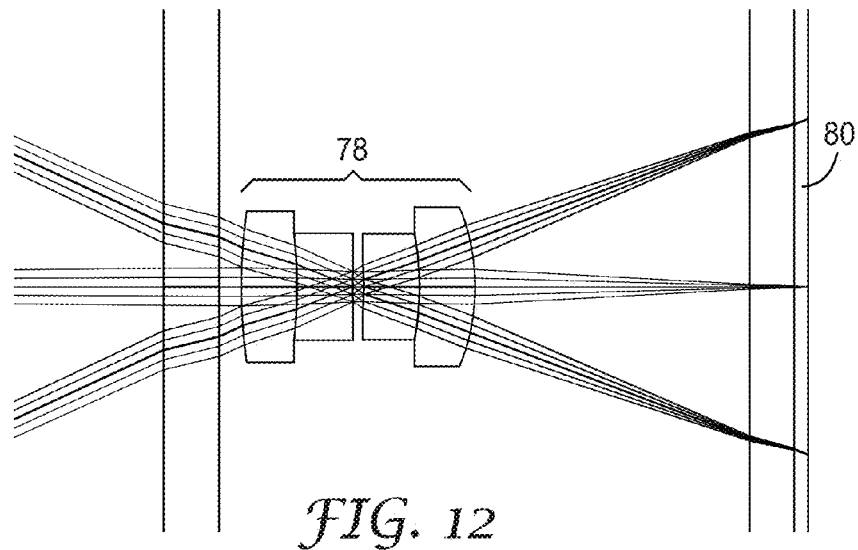
FIG. 12 is a diagram illustrating four optical elements for each optical channel in a 3D imager.

Each of the optical channels in the 3D imagers can have single or multiple optical elements. Multiple elements can achieve superior imaging quality, large depth of field, and athermalized system design. FIGS. 10-12 illustrate three options of the optics for each channel. FIG. 10 illustrates two lenses 70 positioned along an optical path normal to an image sensor 72. FIG. 11 illustrates three lenses 74 positioned along an optical path normal to an image sensor 76. FIG. 12 illustrates four lenses 78 positioned along an optical path normal to an image sensor 80.

Figure 13:
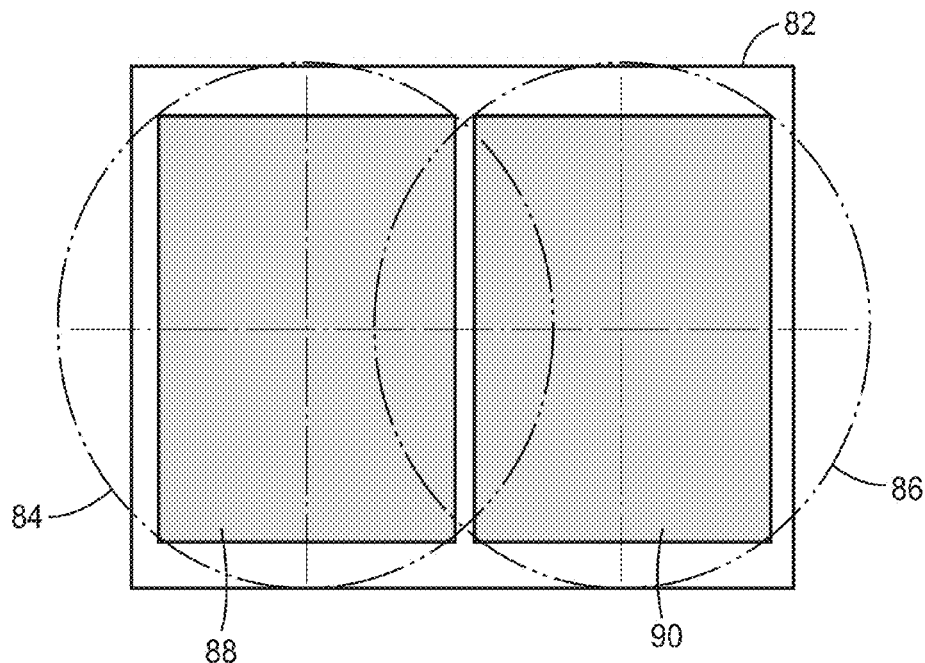
FIG. 13 is a diagram illustrating two image data regions on an image sensor in a 3D imager for obtaining multiple views in a 3D system.
Figure 14:
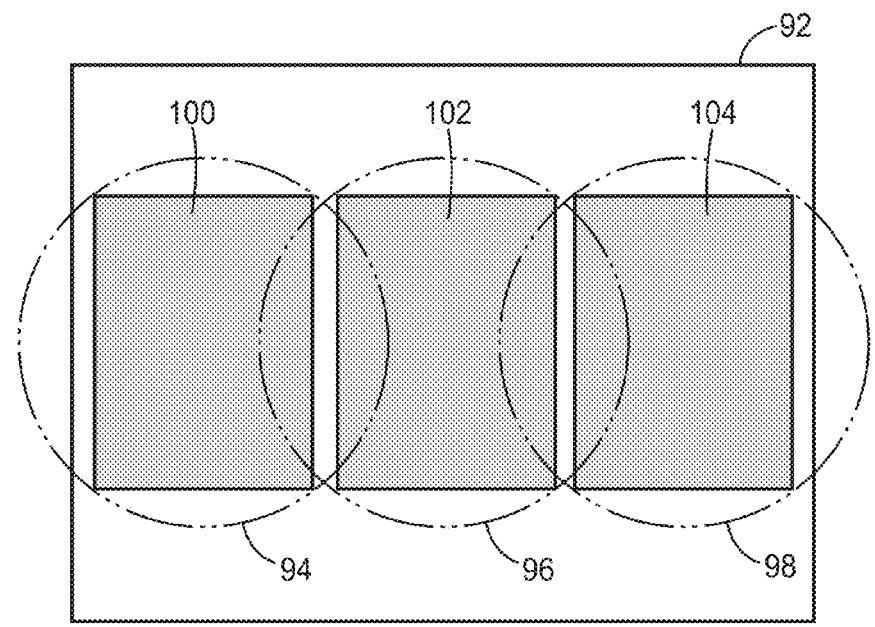
FIG. 14 is a diagram illustrating three image data regions on an image sensor in a 3D imager for obtaining multiple views in a 3D system.

The images of the object formed on the image sensor are located in two regions as shown in FIG. 13 for a two channel system or three regions as shown in FIG. 14 for a three-channel system. In FIG. 13, a first view-angle image 84 is captured in region 88 of an image sensor 82, and second view-angle image 86 is captured in region 90 of image sensor 82. In FIG. 14, a first view-angle image 94 is captured in region 100 of an image sensor 92, a second view-angle image 96 is captured in region 102 of image sensor 92, and a third view-angle image 98 is captured in region 104 of image sensor 92.

The image sensors can be implemented with, for example, any digital imager such as a CMOS or CCD sensor. The image sensor can include a single sensor, as shown, partitioned into multiple image data regions. Alternatively, the image sensor can be implemented with multiple sensors with the image data regions distributed among them.

The invention claimed is:

1. A 3D imaging apparatus, comprising:
   a housing;
   an image sensor within the housing;
   a first mirror and a second mirror each within the housing, the first and second mirrors positioned to receive an image from an object external to the housing and provide the image to the image sensor;
   an aperture element having a plurality of apertures, located along an optical path between the object and the image sensor, for providing the image along a plurality of optical channels corresponding with the apertures to the image sensor;
   a lens positioned within each of the optical channels between the aperture element and the image sensor; and
   a holder within the housing for holding the first mirror, the aperture element, and the lens for each of the optical channels, wherein the holder is located adjacent the image sensor,
   wherein the image sensor is positioned substantially parallel to an object plane of the object,
   wherein a depth of field of the apparatus includes the housing,
   wherein the apparatus is configured to be placed directly on the object to be imaged for intra-oral scanning.

2. The 3D imaging apparatus of claim 1, wherein the housing further comprises a transparent cover positioned within the optical path, and further comprising a light source adjacent the cover for illuminating the object.

3. The 3D imaging apparatus of claim 1, wherein the housing includes an angled tip, and the second mirror is located adjacent an interior surface of the angled tip.

4. The 3D imaging apparatus of claim 1, wherein the image sensor comprises a single image sensor partitioned into multiple regions corresponding with the plurality of optical channels.

5. The 3D imaging apparatus of claim 1, wherein the aperture element is located between the first and second mirrors and the image sensor.

6. The 3D imaging apparatus of claim 1, wherein the first and second mirrors each comprise planar mirrors.

7. The 3D imaging apparatus of claim 1, wherein at least one of the first and second mirrors comprises a concave mirror.

\* \* \* \* \*